(12) United States Patent
Watanabe et al.

(10) Patent No.: US 6,692,698 B1
(45) Date of Patent: Feb. 17, 2004

(54) CHEMICAL REACTION PROCESSING APPARATUS

(75) Inventors: Mamoru Watanabe, Tsukuba (JP); Ikuo Yanase, Tokyo (JP); Takayoshi Sasaki, Tsukuba (JP); Takugo Ootaki, Matsudo (JP)

(73) Assignees: Hitachi High-Technologies Corporation, Tokyo (JP); National Institute for Materials Science, Tsukuba (JP)

( * ) Notice: Subject to any disclaimer, the term of this patent is extended or adjusted under 35 U.S.C. 154(b) by 0 days.

(21) Appl. No.: 09/521,765

(22) Filed: Mar. 9, 2000

(30) Foreign Application Priority Data

Feb. 8, 2000 (JP) ........................................ 2000-030320

(51) Int. Cl.$^7$ ............................................. G01N 23/20
(52) U.S. Cl. .............................. 422/63; 378/71; 436/43
(58) Field of Search ............................... 422/63–65, 67, 422/100; 436/43, 47–48, 180, 174; 378/71

(56) References Cited

U.S. PATENT DOCUMENTS

| 4,391,774 A | * | 7/1983 | Dupain ......................... 422/63 |
| 4,835,707 A | * | 5/1989 | Amano et al. ............... 700/266 |
| 4,846,292 A | * | 7/1989 | Narukawa ..................... 177/50 |
| 4,849,175 A | * | 7/1989 | Dupain et al. ................. 422/63 |
| 4,876,904 A | * | 10/1989 | Limon ........................... 73/866 |
| 5,363,885 A | * | 11/1994 | McConnell et al. ............ 141/1 |
| 5,896,297 A | * | 4/1999 | Valerino, Sr. ................ 700/213 |
| 5,968,731 A | * | 10/1999 | Layne et al. ..................... 435/5 |

OTHER PUBLICATIONS

A Combinatorial Approach to Materials Discovery; X. D. Xiang, Xiaodong Sun, Gabriel Brinceno, Yulin Lou, Kai–An Wang, Hauyee Chang, William G. Wallace–Freedman, Sung–Wei Chen, Peter G. Schultz, Scienc; Jun. 23, 1995; pp. 1738–1740.
Quantum Functional Oxides and Combinatorial Chemistry; Solid State Ionics; Hideomi Koinuma; 1998; pp. 1–7.
Combinatorial Material Libraries on the Microgram Scale with an Example of Hydrothermal Synthesis; Jens Klein, Christian W. Lehmann, Hans–Werner Schmidt and Wilhelm F. Maier; Angew. Chem. International Edition 1998; pp. 3367–3372.

* cited by examiner

*Primary Examiner*—Jan Ludlow
(74) *Attorney, Agent, or Firm*—Omori & Yaguchi USA, LLC

(57) ABSTRACT

The present invention relates to a chemical reaction processing apparatus for producing and analyzing a plurality of samples, including a measuring and mixing section for producing the samples in different mixing ratios by mixing raw inorganic materials and for arranging the samples in predetermined quantities on a reaction tray, a heating apparatus section for heat-treating the samples on the reaction tray all at once, an X-ray diffracting apparatus section for sequentially performing the X-ray diffraction measurement on the samples on the reaction tray, and a collating and analyzing apparatus section for analyzing measurement results obtained in the X-ray diffraction apparatus section.

5 Claims, 3 Drawing Sheets

100

CHEMICAL REACTION PROCESSING APPARATUS

BACKGROUND OF THE INVENTION

1. Field of the Invention

The present invention relates to a chemical reaction processing apparatus and a chemical reaction processing method capable of obtaining many products by means of a combinatorial method, for example, and efficiently analyzing properties of these many products, and to a measuring and mixing apparatus used for the above apparatus and method.

2. Description of the Related Art

The crystal structure, composition, and crystal grain size of ceramic materials can now be controlled on a micron- to nano-scale due to the recent progress in fine ceramics technology. The application range of ceramic materials to electronic components is therefore rapidly widening.

Especially, metal oxide has a wide variety of solid state properties such as dielectric properties, magnetic properties, and electric conductive properties. Because of the various properties of ceramic materials including non-stoichiometry and anisotropy of the crystal structure, there are many parameters to control during the ceramic materials fabrication.

In a conventional method in which materials are produced one by one and their properties are individually examined, it takes a tremendous amount of time to obtain desired materials. A key to exploring new ceramic materials is systematic control of various combinations of a wide variety of raw materials.

SUMMARY OF THE INVENTION

The present invention is made in view of the above situation, and an object of the present invention is to provide a chemical reaction processing apparatus and a chemical reaction processing method capable of obtaining various chemical products with easy control and efficiently analyzing and evaluating them, and to provide a measuring and mixing apparatus used for the above apparatus and method.

To attain the above object, a first main aspect of the present invention is a chemical reaction processing apparatus for producing a plurality of samples, each sample obtained by mixing a plurality of raw inorganic materials in its own predetermined mixing ratio, and for analyzing the samples, comprising: a measuring and mixing section for producing the samples and for arranging the samples in respective predetermined quantities on a reaction tray; a heat treating section for heat-treating the samples on the reaction tray all at once; a measurement section for sequentially performing a predetermined measurement on the samples on the reaction tray; and an analyzing section for analyzing measurement results obtained in the measurement section.

According to the aforesaid configuration, various products can be obtained at a time by a combinatorial method, and these products can be analyzed and evaluated efficiently.

It is preferable that the aforesaid raw materials are in the form of a slurry or a liquid.

The measuring and mixing section comprises a raw material distribution mechanism wherein each raw material is measured by volume and is distributed in predetermined quantities into mixing vessels, in which the raw inorganic materials are mixed to produce the samples.

According to the aforesaid configuration, each raw material can be measured by means of pipette suction or discharge volume; therefore, the composition and distribution can be easily controlled. Moreover, the use of slurry-like raw materials makes mixing of raw materials efficient. It is preferable that the measuring and mixing section includes an agitating means in order to make the mixtures as uniform as possible.

Further, it is preferable that the measuring and mixing section includes a mixing vessel holding section for holding the mixing vessels in which the raw materials are distributed and mixed.

The measuring and mixing section further comprises a sample transfer mechanism for transferring the samples from the mixing vessels to the reaction tray on which the samples are arranged in respective predetermined quantities.

According to the aforesaid configuration, the raw materials are transferred to the reaction tray after being mixed once in the mixing vessels, whereby mixing of the materials can be made more effectively than the case wherein the raw materials are directly distributed to the reaction tray and mixed therein.

Furthermore, it is preferable that the samples in all the mixing vessels have approximately the same volume as well as approximately the same total number of moles of the elements of the raw materials. As a result, samples even with different molar fractions of raw materials have approximately the same number of moles per unit volume. Thus, measurement conditions can be adjusted easily even for different samples in the analyzing process.

It is preferable that the transfer of the samples to the reaction tray is made over a plurality of times each in a small quantity, so that the samples can be dried fast.

Furthermore, the apparatus comprises a flattening means for flattening the surfaces of the samples on the reaction tray. The flattening means preferably comprises a press-molding plate for pressing the samples to make the sample surfaces almost flat. As a result, measurements in the measurement section can be performed accurately. Instead of the press-molding plate, a cutting means may be used as the flattening means for cutting off heaped portions of the samples to make the sample surfaces almost flat.

A second main aspect of the present invention is a measuring and mixing apparatus for producing a plurality of samples, each sample obtained by mixing a plurality of raw inorganic materials in its own predetermined mixing ratio, comprising: a raw material distribution means wherein each raw inorganic material is measured by volume and is distributed in predetermined quantities into mixing vessels in which the raw inorganic materials are mixed to produce the samples; and a sample transfer means for transferring the samples from the mixing vessels to a reaction tray on which the samples are arranged in respective predetermined quantities. It is preferable that this measuring and mixing apparatus is used for the chemical reaction processing apparatus according to the first aspect of the present invention, and it is more preferable that the measuring and mixing apparatus includes the aforesaid characteristics of the measuring and mixing section of the chemical reaction processing apparatus.

A third aspect of the present invention is a chemical reaction processing method for producing a plurality of samples, each sample obtained by mixing a plurality of raw inorganic materials in its own predetermined mixing ratio, and for analyzing the samples, comprising: a measuring and mixing step of producing the samples and of arranging the samples in respective predetermined quantities on a reaction tray; a heat treating step of heat-treating the samples on the reaction tray all at once; a measurement step of sequentially performing a predetermined measurement on the samples on the reaction tray; and an analyzing step of analyzing measurement results obtained in said measurement step.

According to the aforesaid configuration, various products can be obtained at a time by a combinatorial method, and these products can be analyzed and evaluated efficiently.

Other characteristics and remarkable effects of the present invention will become apparent to those skilled in the art upon reading the following specification when taken in conjunction with the accompanying drawings.

DETAILED DESCRIPTION OF THE PREFERRED EMBODIMENT

A combinatorial synthesizing system as a preferred embodiment of the present invention is explained below with reference to the drawings.

Figure 1:
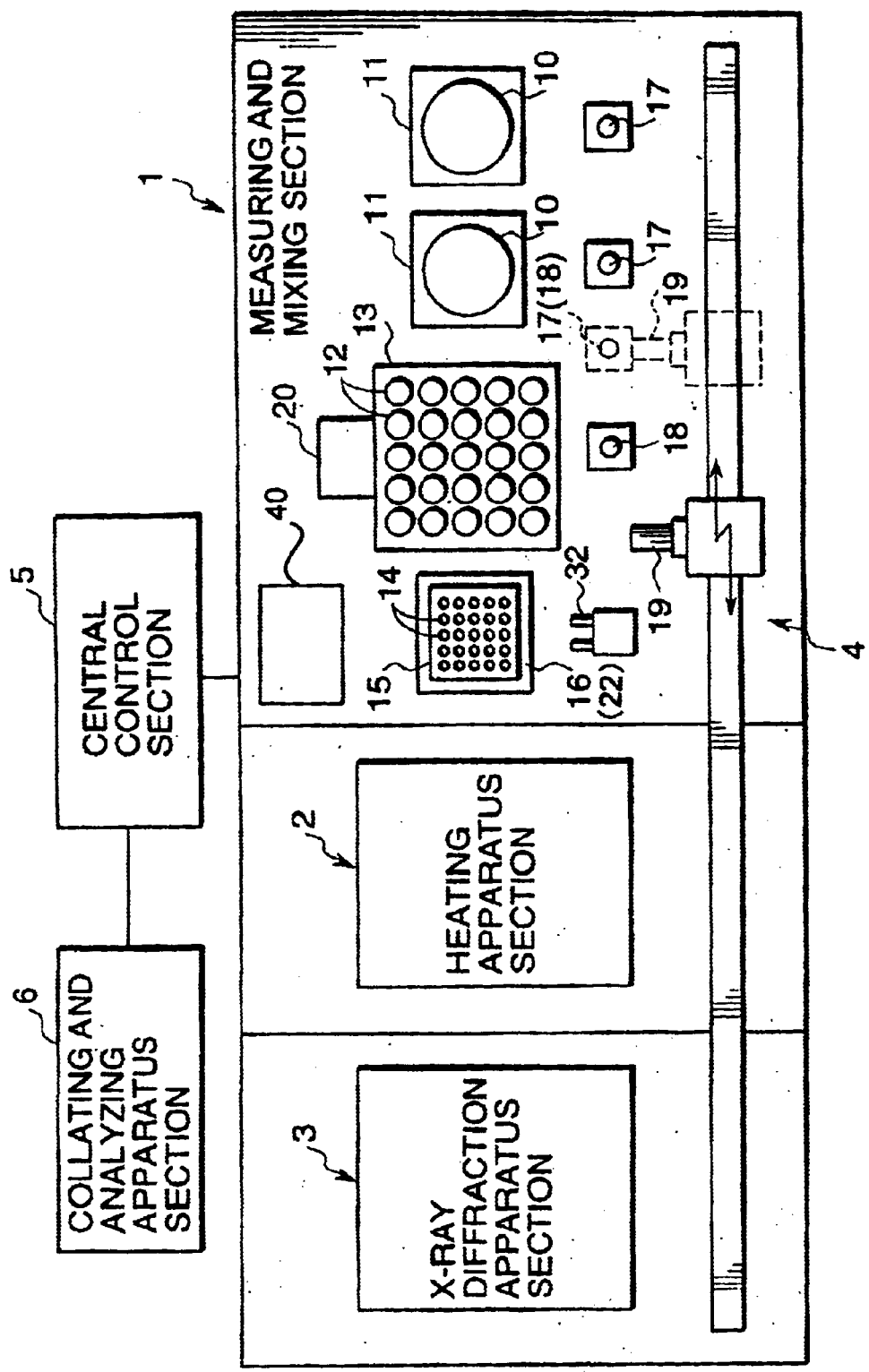
FIG. 1 is a schematic block diagram showing an embodiment of the present invention.

As shown in FIG. 1, the system is comprised of a measuring and mixing section 1 for volume-measuring, distributing, and mixing inorganic raw materials to produce samples; a heating apparatus section 2 for heat-treating the samples; an X-ray diffraction apparatus section 3 for performing an X-ray diffraction measurement on the heat-treated samples; and a transport mechanism 4 for transporting the samples from the section 1 through 3. The system further includes a central control section 5, which automatically controls operations such as measuring the raw materials by volume, distributing them to mixing vessels, mixing the materials in the mixing vessels to produce the samples, transferring the samples to a reaction tray, controlling atmosphere, heat-treating the samples, and performing the X-ray diffraction measurement on the samples. The central control section 5 is connected to a data collating and analyzing apparatus section 6, which carries out the task of phase identification and generates reaction diagrams by collating the obtained data with a database.

Figure 2:
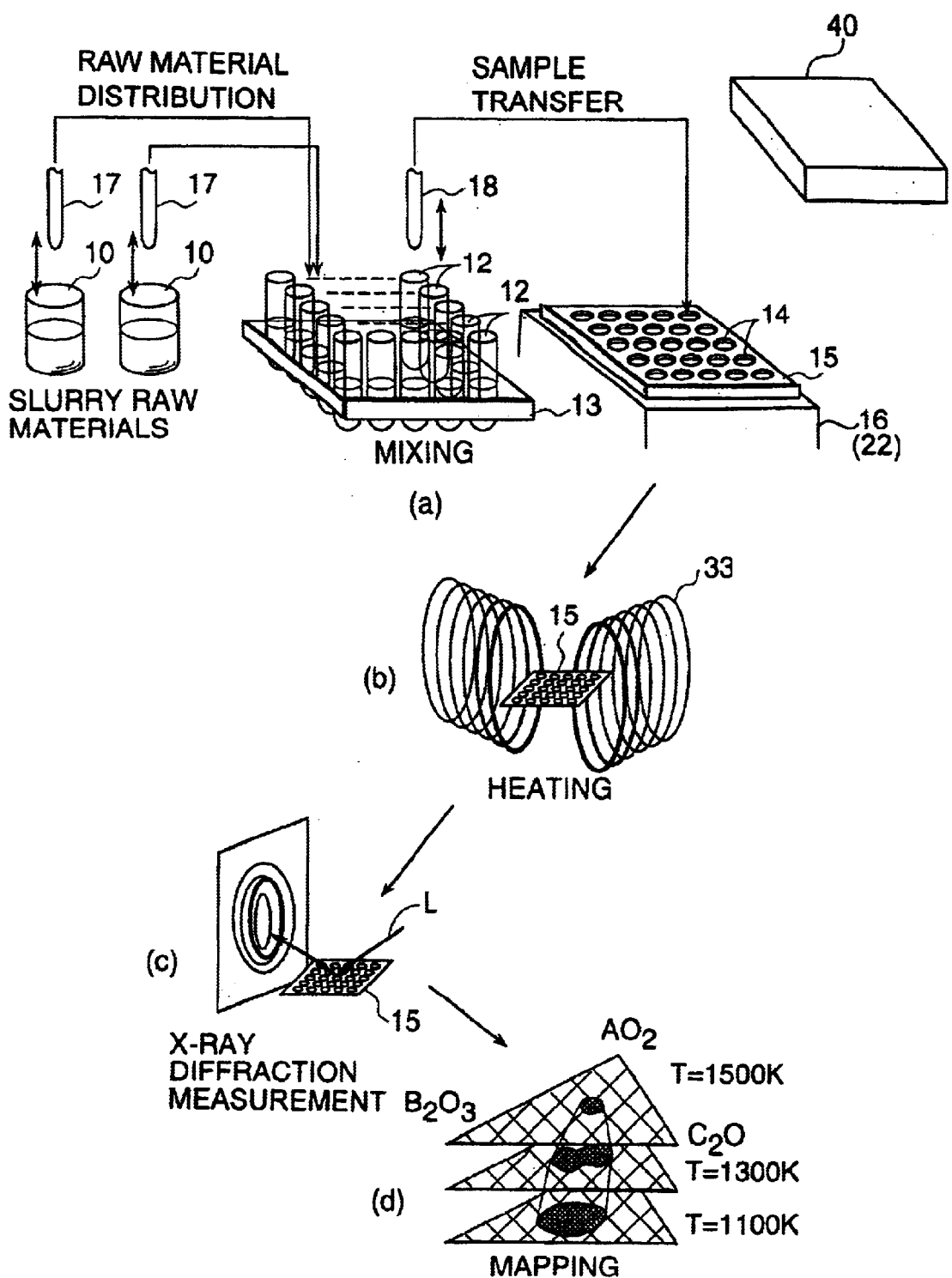
FIGS. 2(a)–(d) are schematic diagrams each showing a processing step.
Figure 3:
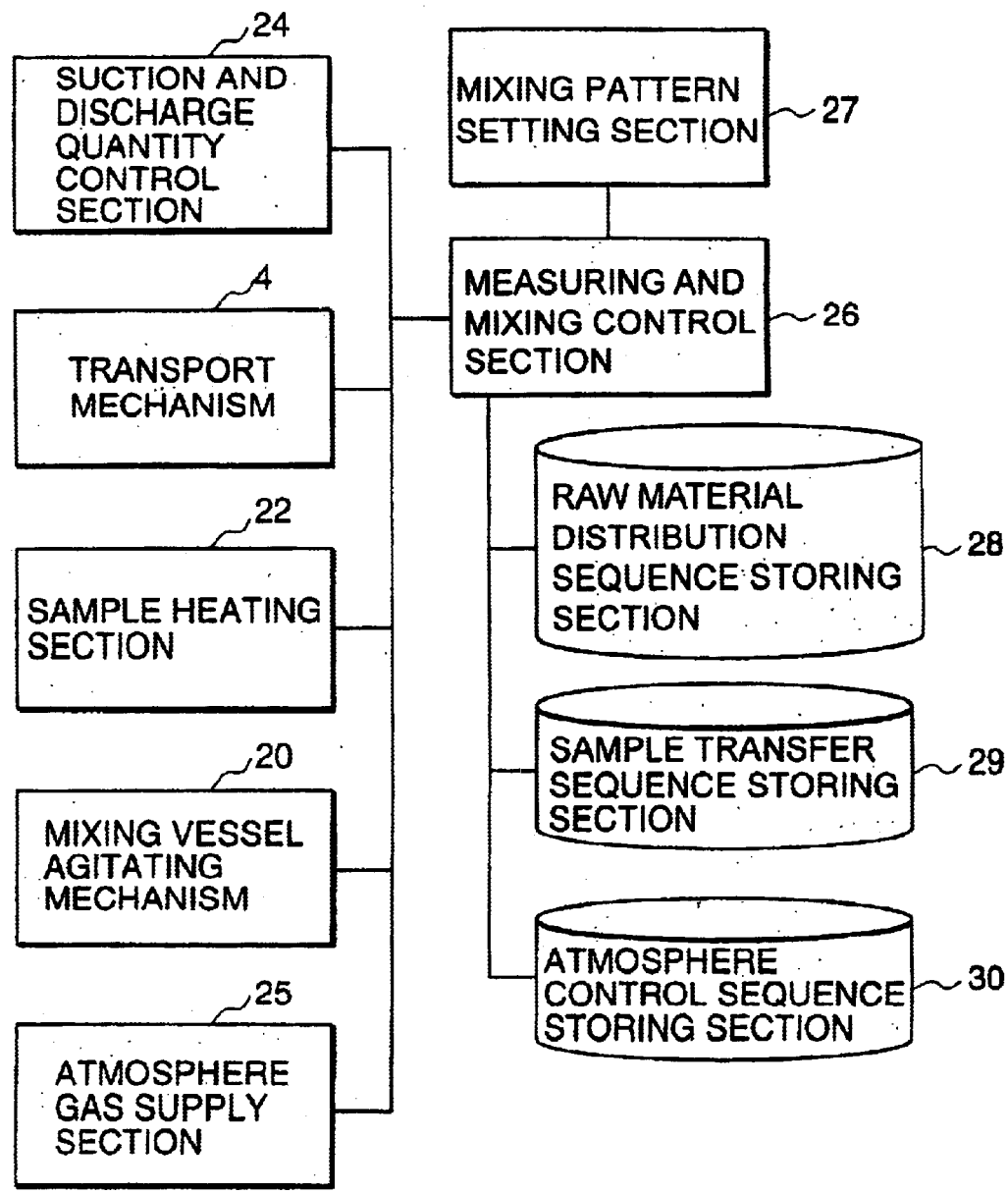
FIG. 3 is a block diagram showing the system configuration of a measuring and mixing section.

FIGS. 2(a)–(d) are diagrams schematizing the processing steps in the aforesaid system, and FIG. 3 is a block diagram showing a control system for the measuring and mixing section 1. Each of these components is explained in detail below with reference to FIGS. 1–3.

As shown in FIG. 1, the measuring and mixing section 1 includes: a plurality of raw material bottle holding sections 11, each for holding a raw material bottle 10 which contains a slurry-like raw material; a mixing vessel holding section 13 for holding a plurality of mixing vessels 12 (test tubes, for example) in which the raw materials are distributed and mixed to produce samples in different predetermined mixing ratios; and a reaction tray holding section 16 for holding a reaction tray 15 having a plurality of recessed portions 14 to which the samples in the mixing vessels 12 are respectively transferred. In the present embodiment, as shown in FIG. 1 and FIG. 2(a), twenty-five mixing vessels 12 are prepared so that 25 different samples with respective mixing ratios of raw materials can be made. The reaction tray 15 has 25 recessed portions 14, each having a predetermined capacity, corresponding to the number of the mixing vessels 12.

Further, the measuring and mixing section 1 includes: raw material distribution pipettes 17, each moving from one of the raw material bottles 10 to the mixing vessels 12; and a sample transfer pipette 18 moving between the mixing vessels 12 and the reaction tray 15 by means of the transport mechanism 4. The raw material distribution pipettes 17 and the sample transfer pipette 18 are detachably held by a head 19 of the transport mechanism 4 as shown by dotted line in FIG. 1.

Furthermore, an agitating mechanism 20 for performing agitation by giving vibration to the mixing vessels 12 is attached to the mixing vessel holding section 13. A heating element 22 such as a heater is provided in the reaction tray holding section 16. A hand 32, detachably attached to the head 19 of the transport mechanism 4, for gripping and transporting the reaction tray 15 is provided at a position opposite to the reaction tray holding section 16.

As described later in detail, a flattening means 40 such as a press-molding plate is provided for flattening surfaces of the samples. This flattening means can be placed anywhere as long as the flattening operation can be performed before the X-ray diffraction measurement.

FIG. 3 is a block diagram showing the control system for the measuring and mixing section 1. A suction and discharge quantity control section 24 is connected to the raw material distribution pipettes 17 and the sample transfer pipette 18, and controls the suction and discharge quantities of these pipettes. An atmosphere gas supply section 25 continuously supplies, for example, dry air at a predetermined temperature in order to suitably control atmosphere inside the measuring and mixing section 1. The atmosphere gas supply section 25 can also control atmosphere in the heating apparatus section 2 and the X-ray diffraction apparatus section 3 individually.

Further, a measuring and mixing control section 26 shown in FIG. 3 is provided in the central control section 5. A mixing pattern setting section 27, a raw material distribution sequence storing section 28, a sample transfer sequence storing section 29, and an atmosphere control sequence storing section 30 are connected to the measuring and mixing control section 26. In the mixing pattern setting section 27, mixing ratios of the raw materials, determined by means of molar fractions, are stored for the respective mixing vessels 12 (explained in detail later). In the raw material distribution sequence storing section 28 and the sample transfer sequence storing section 29, movement routes of the pipettes 17 and 18 during the raw material distribution and sample transfer operations are respectively stored. In the atmosphere control sequence storing section 30, operation timing of the atmosphere gas supply section 25 is stored.

The operation of each section is explained in detail below.

First, the raw material distribution operation is explained as follows. As shown in FIG. 2(a), by use of one of the raw material distribution pipettes 17, each raw material is extracted from its own raw material bottle 10 and is distributed into the mixing vessels 12 in predetermined quantities. This operation is repeated for all the raw materials to produce samples in the mixing vessels 12 in different mixing ratios. In this embodiment, slurry-like raw materials are used; therefore, these raw materials can be measured by the suction and discharge volume of the pipettes 17 and 18.

In the above description, "slurry" means a fluid substance suspended with fine solid particles (with a particle diameter of several ten nanometers to several hundred nanometers). The slurry used in the present embodiment is metal oxide ($TiO_2$, $SnO_2$, $Al_2O_3$, for example), which resembles a slurry obtained by adding water to clay. In this embodiment, it is preferable that the raw material slurry is composed of metal oxide particles with a particle diameter of 30 nm to 100 nm (1 mm=$10^6$ nm) suspended in water or organic solvent (ethanol, for example). The concentration of the raw material slurry used in this embodiment is 40 wt % maximum (for example, 60 g of water+40 g of oxide) and 5 wt % minimum approximately.

When different sorts of raw material slurry are mixed, aggregation of different sorts of fine particles commonly occurs, making it difficult to obtain a homogeneous slurry. In this embodiment, the agitating mechanism 20 is provided in order to overcome the above disadvantage. Aggregation may also be prevented by application of supersonic waves, bubbling of inactive gas, or a chemical method (for example, addition of a special surfactant) instead of the above mechanical agitation.

When the raw materials are measured by means of the discharge volume of the pipettes 17, the minimum discharge volume should be beyond its measurement error so that a significant difference in mixing profile can be obtained between the two samples with the closest mixing ratios. Thus, accuracy of the discharge volume measurement as well as increments in values of the mixing ratios should be taken into consideration in determining the minimum discharge volume.

In order to easily obtain samples with approximately the same volume, the molarity of an element needs to be made equal for all the raw materials prior to mixing. This can be arranged as follows. Let the elements be A, B, . . . , and M, the chemical formulas of the corresponding oxides, i.e. raw materials, be $A_xO_y$, $B_qO_p$, . . . , and $M_rO_s$, and their formula weights be Ma, Mb, . . . , Mm. The concentration of each of the raw materials should be adjusted so that Ma/x=Mb/q= . . . =Mm/r can hold. When the raw materials are prepared in this fashion, the volume can be made approximately the same for all the samples after mixing, while at the same time the total number of moles of the elements can be made approximately the same in all the samples. The above preparation greatly simplifies the distribution process while providing highly accurate control, and also makes synthesizing operations tractable.

The sample transfer process is explained as follows. In this process, the samples obtained in the mixing vessels 12 are extracted with the sample transfer pipette 18 and transferred to the respective recessed portions 14 on the reaction tray 15. During this process, in order to sufficiently dry the samples, each sample is transferred over several times each in a small quantity, while the reaction tray 15 is heated at a temperature of 80° C. to 200° C. by the heating section 22 to accelerate drying.

After all the samples, each in a necessary quantity, are transferred to the respective recessed portions 14, a small quantity of ethanol is dropped onto each sample. Thereafter, a flattening means 40 such as a press-molding plate is moved onto the reaction tray 15, and the samples in all the recessed portions 14 are collectively press-molded, whereby the upper surfaces of the samples are molded flat and smooth.

In other words, the samples are arranged into the respective recessed portions 14 in such a manner that rice is served in bowls. Thereafter, the heaped samples are pressed with a press-molding plate, for example, so that the sample surfaces are flattened. Since the samples are hard to mold after being dried, a small quantity of alcohol or the like is dropped onto each of the heaped samples to provide pliability thereto, and then the samples are pressed. Incidentally, it is desirable that all the samples in the recessed portions 14 have approximately the same top level. Hence, it is preferable that the degree of heaping is adjusted to be approximately the same in all the recessed portions 14 during the time of sample transfer, so that press molding can be collectively carried out.

It should be mentioned that the aforesaid dropping of ethanol and flattening are performed to obtain evenness and smoothness of the surfaces of the samples necessary for the X-ray diffraction measurement. Accordingly, the flattening operation may be performed at any point before the X-ray diffraction apparatus section 3. (As an example, FIGS. 1 and 2 show the case wherein the flattening means 40 such as a press-molding plate is in the measuring and mixing section 1.) Further, the samples may be made pliable by other means than dropping of ethanol. When pliability is not required, press molding may be carried out without dropping of ethanol or the like. Furthermore, the surfaces of the samples may be flattened by cutting off the heaped portions of the samples instead of press molding.

The heat-treating process by the heating apparatus section 2 is explained as follows. After the sample transfer and the flattening operation, the transport mechanism 4 grips the reaction tray 15 by use of the hand denoted by 32 in FIG. 1, and then transports the reaction tray 15 to the heating apparatus section 2.

The heating apparatus section 2 is a synthesizing furnace to heat-treat a group of samples in a predetermined atmosphere at a synthesizing temperature for a certain reaction time. Specifically, as shown in FIG. 2(b), the reaction tray 15 is placed and heated in a heating coil 33.

It should be noted that a plurality of reaction trays 15 may be collectively heat-treated. For example, when the number of raw materials, that is, the number of components is three, 66 combinations can be obtained when the mixing ratios of the components are given in increments of 0.1 between zero and one. Hence, it is desirable in terms of efficiency that they are collectively heat-treated under the same condition of the reaction temperature, atmosphere, and so on.

The heating of the reaction tray 15 is not limited to the method in which a heating coil is used, but other methods, such as high-frequency heating or heating with a ceramic element, may be employed.

After the heat-treating process in the heating apparatus section 2, the transport mechanism 4 grips the reaction tray 15 using the hand 32 and then moves it to the X-ray diffraction apparatus section 3.

After the reaction tray 15 is moved to a predetermined sample measurement position and fixed therein, the X-ray diffraction apparatus section 3 sequentially adjusts the sample positions on the reaction tray 15 so as to expose them to an incident X-ray beam L as shown in FIG. 2(c). After the X-ray diffraction measurement, the collected data are converted into such a form that the data can be collated with a JCPDS file. (The JPCDS is a well-known X-ray diffraction data file.) The data is outputted with one-to-one correspondence to the samples on the reaction tray.

The outputted data is sent to the collating and analyzing apparatus section 6 via the central control section 5, where analysis and collation thereof are performed.

Specifically, the collating and analyzing apparatus section 6 collates the X-ray diffraction data (X-ray intensity as a function of diffraction angle) obtained for each of the samples with the existing data file (JCPDS file), and extracts already known phases and diffraction patterns of unknown phases. The collating and analyzing apparatus section 6 performs this operation for all the samples on the reaction tray 15, plots the analysis and collation results in n-dimensional space with the number of raw materials as n, and draws, registers, and prints reaction diagrams as shown in FIG. 2(*d*).

The reaction diagram is explained as follows with reference to FIG. 2(*d*). When A1, A2, A3, . . . An are elements, and oxides thereof are represented by A1O, A2O$_2$, A3$_2$O$_3$, . . . AnO$_2$, this diagram forms an n-dimensional coordinate system with the molar fraction of each of Am$_x$O$_y$ (M: 1 to n, x: 1 or 2, y: 1 or 2 or 3) on a coordinate axis. Thus, each point of the n-dimensional coordinate corresponds to a certain mixing ratio expressed by the molar fractions. The X-ray diffraction result for each sample with its own mixing ratio is mapped at the corresponding point of the n-dimensional coordinate, thereby generating a reaction diagram. This procedure is repeated for different heat-treating temperatures. As an example, FIG. 2(*d*) shows a case with n=3, having three oxides of AO$_2$, B$_2$O$_3$, and C$_2$O for the raw materials, and for the temperatures of T=1100K, 1300K, and 1500K.

As described above, according to the present invention, various products by a combinatorial method can be obtained with easy control, and a synthesizing and analyzing apparatus capable of efficiently analyzing and evaluating these products can be provided.

Further, according to this embodiment, raw materials can be measured by the suction or discharge volume by use of the pipettes 17; therefore, the composition and distribution can be easily controlled. Also, the use of slurry-like raw materials makes mixing of raw materials efficient.

Furthermore, as in the aforesaid embodiment, when the molarity of an element is made equal for all the raw materials, the samples made from raw materials even with different molar fractions will result in having approximately the same total number of moles of the elements per unit volume. Thus, measurement conditions can be adjusted easily even for different samples in the analyzing process.

The transfer of the samples to the reaction tray 15 is made over several times each in a small quantity so that the samples can be dried fast and have high quality after heat-treating.

It should be mentioned that the present invention is not limited to the aforesaid embodiment, and various changes may be made therein without departing from the spirit of the present invention.

For example, although the transport mechanism is provided with the head moving linearly in the aforesaid embodiment, it may be provided with a head moving in the X-, Y-, and Z-directions or in the θ-, R-, and Z-directions (a cylindrical coordinate system).

Further, any number of raw materials can be handled by this invention.

Furthermore, although the raw materials in the form of a slurry are used in the aforesaid embodiment, materials such as metallic alcoxide, wherein good mixing can be obtained by dissolving it in a solvent such as water or alcohol, may be used. Also, metal or oxide fine particles with a particle diameter of several ten nanometers to several hundred nanometers, wherein good mixing can be obtained by adding an appropriate solution, may be used.

In the aforesaid embodiment, the ceramic combinatorial synthesizing apparatus is explained as an example. The present invention is not limited to the aforesaid embodiment, and can be widely applicable for various chemical reaction processing. For example, the function of the aforesaid measuring and mixing section can be applied to batch processing of optimization of acidizing conditions for powdered substances, autoplastic reaction processing, and so on.

What is claimed is:

1. A chemical reaction processing apparatus for producing a plurality of samples, each sample obtained by mixing a plurality of raw inorganic materials in its own predetermined mixing ratio, and for analyzing the samples, comprising:

a measuring and mixing section including (A) a raw material distribution mechanism wherein each raw inorganic material is measured by volume and is distributed in predetermined quantities into mixing vessels, in which the raw inorganic materials are mixed to produce the samples, and (B) a sample transfer mechanism for transferring the samples from the mixing vessels to a reaction tray on which the samples are arranged in respective predetermined quantities;

a flattening means for flattening surfaces of the samples on the reaction tray;

a heat treating section for heat-treating the samples on the reaction tray all at once;

a measurement section for sequentially performing a predetermined measurement on the samples on the reaction tray; and an analyzing section for analyzing measurement results obtained in said measurement section.

2. The chemical reaction processing apparatus as set forth in claim 1, wherein said measuring and mixing section includes a mixing vessel holding section for holding said mixing vessels in which the raw materials are distributed and mixed to produce the samples.

3. The chemical reaction processing apparatus as set forth in claim 2, wherein said measuring and mixing section includes an agitating means, connected to said mixing vessel holding section, for agitating the samples in the mixing vessels.

4. The chemical reaction processing apparatus as set forth in claim 1, wherein said flattening means comprises a press-molding plate for pressing the samples on the reaction tray to make the sample surfaces flat.

5. The chemical reaction processing apparatus as set forth in claim 1, wherein said flattening means comprises a cutting means for cutting off heaped portions of the samples on the reaction tray to make the sample surfaces flat.

\* \* \* \* \*